US010556000B2

(12) United States Patent
Gill et al.

(10) Patent No.: US 10,556,000 B2
(45) Date of Patent: Feb. 11, 2020

(54) THERMOSTABLE SPRAY DRIED ROTAVIRUS VACCINE FORMULATION AND PROCESS THEREOF

(71) Applicant: MSD WELLCOME TRUST HILLEMAN LABORATORIES PVT. LTD., New Delhi (IN)

(72) Inventors: Davinder Gill, New Delhi (IN); Nitin Saigal, New Delhi (IN); Sachin Kale, Haryana (IN); Tarun Sharma, New Delhi (IN); Nidhi Shukla, Uttar Pradesh (IN); Deepa Sikriwal, New Delhi (IN); Robert Evans, Sourderton, PA (US)

(73) Assignee: MSD WELLCOME TRUST HILLEMAN LABORATORIES PVT. LTD., New Delhi (IN)

( * ) Notice: Subject to any disclaimer, the term of this patent is extended or adjusted under 35 U.S.C. 154(b) by 171 days.

(21) Appl. No.: 15/327,102

(22) PCT Filed: Jul. 17, 2015

(86) PCT No.: PCT/IB2015/055427

§ 371 (c)(1),
(2) Date: Jan. 18, 2017

(87) PCT Pub. No.: WO2016/009400

PCT Pub. Date: Jan. 21, 2016

(65) Prior Publication Data

US 2017/0173145 A1 Jun. 22, 2017

(30) Foreign Application Priority Data

Jul. 18, 2014 (IN) .......................... 2039/DEL/2014

(51) Int. Cl.

| | |
|---|---|
| ***A61K 39/15*** | (2006.01) |
| ***A61K 39/12*** | (2006.01) |
| ***A61K 9/16*** | (2006.01) |
| ***C12N 7/00*** | (2006.01) |
| *A61K 39/00* | (2006.01) |

(52) U.S. Cl.

CPC ............ *A61K 39/15* (2013.01); *A61K 9/1611* (2013.01); *A61K 9/1617* (2013.01); *A61K 9/1623* (2013.01); *A61K 9/1652* (2013.01); *A61K 9/1682* (2013.01); *A61K 39/12* (2013.01); *C12N 7/00* (2013.01); *A61K 2039/51* (2013.01); *A61K 2039/525* (2013.01); *A61K 2039/70* (2013.01); *C12N 2720/12334* (2013.01); *C12N 2720/12351* (2013.01)

(58) Field of Classification Search

None

See application file for complete search history.

(56) References Cited

U.S. PATENT DOCUMENTS

| | | | | |
|---|---|---|---|---|
| 6,616,931 | B1 * | 9/2003 | Burke | A61K 39/15 424/215.1 |
| 2007/0154404 | A1 * | 7/2007 | Colombo | A61K 9/0075 424/46 |
| 2011/0154404 | A1 | 6/2011 | Piepenbrink et al. | |
| 2011/0243988 | A1 * | 10/2011 | Ohtake | A61K 39/165 424/212.1 |
| 2011/0244032 | A1 * | 10/2011 | Parikh | A61K 9/145 424/451 |

FOREIGN PATENT DOCUMENTS

WO 2011/098837 A1 8/2011

* cited by examiner

*Primary Examiner* — Shanon A. Foley
*Assistant Examiner* — Myron G Hill
(74) *Attorney, Agent, or Firm* — W&C IP

(57) ABSTRACT

The present invention relates to an improved thermostable spray dried rotavirus vaccine formulation and the process of preparing the same. More specifically the present invention discloses thermostable liquid, powder or granule-based rotavirus vaccine prepared using the spray drying process, such that the said vaccine has improved heat-stability, ease-of-use, ease-of-transportation and affordability features with significantly better chance of being adopted in developing and low income country's vaccination program.

16 Claims, 7 Drawing Sheets

THERMOSTABLE SPRAY DRIED ROTAVIRUS VACCINE FORMULATION AND PROCESS THEREOF

FIELD OF THE INVENTION

The present invention relates to an improved thermostable spray dried rotavirus vaccine formulation and process thereof. The present invention further discloses an improved spray drying process to obtain thermostable (Heat-stable) rotavirus vaccine formulation. The vaccine formulation of the present invention has improved heat-stability, ease-of-use, ease-of-transportation and affordability features with significantly better chances of being successfully adopted in developing and low income country's vaccination program.

BACKGROUND OF THE INVENTION

It is well established that rotaviruses are the leading cause of severe diarrhea among infants and young children. It is estimated that globally 0.6 million children under the age of 5 die annually due to rotavirus diarrhea and another 2 million are hospitalized. 90% of these deaths occur in developing countries. Rotavirus is highly contagious and resistant and, regardless of water quality and available sanitation nearly every child in the world is at risk of infection. A rotavirus vaccine is usually administered to children to protect them from rotavirus infection.

On Jun. 5, 2009, the World Health Organization (WHO) recommended that rotavirus vaccine be included in all national immunization programs. The Rotavirus Vaccine Program and the Accelerated Vaccine Introduction Initiative have worked to study rotavirus vaccines among developing-country populations to assist developing countries in introducing rotavirus vaccines into routine immunization programs. These partnerships are spearheaded by international non-governmental organization PATH, WHO, the U.S. Centres for Disease Control and Prevention, and the Global Alliance for Vaccines and Immunization. International research data suggests that current rotavirus vaccines have 85% to 95% efficacy against severe rotavirus gastroenteritis (RVGE). However, there are concerns while using the same in developing countries where most rotavirus caused deaths occurs, and where access to treatment is limited. One of the main reasons is that immunization schedule for children are neither prepared nor strictly followed in these countries, in spite of the fact that nearly every child in the world will suffer a rotavirus infection before age five. The primary reasons for this are centred on programmatic suitability as well as cost of current vaccines. Programmatic suitability is a new process developed by the WHO for prequalification of vaccines. The prequalification process includes a review of the production process and quality control procedures, review of clinical data, testing of consistency of lots, and a joint WHO and national regulatory authority site visit to the manufacturing facilities. Once the evaluation is complete and if the vaccine is found to be acceptable, in principle, for purchase, it is considered prequalified and is posted on the WHO website.

The existing vaccines are stable only for a limited duration at a particular temperature. It is well known in the art that the vaccine must be stored and transported at refrigeration temperatures maintained at 2° C. to 8° C. Further, it is also well known that vaccines must be administered immediately on being removed from refrigeration. The currently approved vaccine is stable for up to 24 to 36 months at 2° C. to 8° C.

Studies indicate that if one of the presently WHO approved rotavirus vaccine, Rotateq, is inadvertently exposed or stored at temperatures above 8° C., the potency is maintained for the maximum exposure of 48 hours at 9° C. to 25° C. or for a bare 12 hours at 26° C. to 30° C. Indeed if this vaccine is exposed to temperatures above 30° C., or if the time mentioned above has lapsed, the vaccine has to be discarded since it has lost its potency. There is limited data to suggest that if the vaccine is inadvertently exposed to temperatures below 0° C., the potency of the vaccine is maintained.

This necessitates the rotavirus vaccine's strict cold chain storage and transport which is problematic particularly in the developing and low income regions where cold chain required for maintaining vaccine potency and efficacy is imperfect, overburdened or nonexistent, resulting in large amount of vaccine being wasted and in worst case scenario endangering the lives of potential recipients. Reportedly the wastage is as high as 25% to 50%

International patent application number WO2009042202 discloses formulations for preservation of rotavirus. This invention provides formulations and methods for stabilizing viruses in liquid and dried formulations. In particular, formulations are provided including $Zn^{2+}$ cations that stabilize the viability of Rotaviruses. Methods of vaccination include neutralization of gastric contents and administration of the vaccine formulations of the invention.

US patent application number US 20120308526 discloses sonic low pressure spray drying method. This invention provides methods of spray drying pharmaceutical powders from a vibrating nozzle at low pressures. The method can effectively spray dry thick or viscous solutions or suspensions to provide small uniform particles. The invention includes dry particle compositions prepared by methods of low pressure spraying from vibrating nozzles.

In addition to being thermostable, it is also important that vaccine is suitable from programmatic point of view. The vaccine should be easily prepared in its final form, occupy low volume in cold chain and be easy to dispose after use. Most existing solid form of vaccines including freeze dried vaccines as well as spray dried candidate vaccines are packaged in separate containers/components and require syringe and a vial as well as other complex and costly mechanisms for reconstitution and administration. This creates difficulty in the administration of vaccine and also greatly increases the footprint of the vaccine overburdening the cold chain. This also in turn increases the shipping and distribution challenges, logistics for storage and is prone to potentially fatal reconstitution errors like buffer/vaccine mismatch, contamination, administration of wrong volumes or administration by wrong route, etc.

It is clear that primary packaging has greatest influence on above mentioned programmatic aspects. Number of delivery devices are being developed and tested for vaccine administration. In order for successful mating of these diverse and promising delivery device with the vaccine it is crucial that vaccine formulation be designed that offers greatest flexibility of packaging. Commonly used vial lyophilisation method of stabilization generates vaccine cake that offer least amount of flexibility of packaging in drug delivery devices. Even if lyophilisation process is conducted in drug delivery devices such as dual chamber syringes or cartridges devices the cost due to device as well as processing cost be extremely high. For a vaccine to be broadly adopted in low income regions it is crucial to keep the cost of processing and packaging a vaccine low.

Another component that has influence on price of vaccine is stabilizers and excipients that are used in formulation. It is also crucial from the regulatory and safety point of view that excipient's and stabilizers used should contain neither substances of animal origin nor contain animal component. Indeed in some countries, it is not desirable for cultural and religious reasons as well.

Therefore, to cater to the abovementioned problems there is a need of a thermostable, cost-effective vaccine which will be a great advantage to the vaccination program in solving the logistics of delivering vaccines that retain their potency at room temperature and that which can be afforded by the low income and developing world countries.

Object of the Invention

The main object of the invention is to provide an improved thermostable spray dried rotavirus vaccine formulation.

Another object of present invention is to provide a spray drying process to obtain the improved thermostable spray dried rotavirus vaccine formulation.

Yet another object of the present invention is to provide an improved spray drying process to obtain an improved thermostable spray dried rotavirus vaccine formulation using two-fluid nozzle for atomization of the fluid through the nozzle.

Yet another object of present invention is to provide an improved thermostable spray dried rotavirus vaccine formulation that obviates or significantly minimizes potency losses at elevated temperatures for a longer period thereby reducing dependency on refrigeration and cold chain maintenance.

Yet another object of the invention is to provide for a process of preparing an improved thermostable spray dried rotavirus vaccine formulation that comprises of strains of live rotaviruses selected from bovine, rhesus, human, ovine, rhesus/human reassortants, or bovine/human reassortants.

Yet another object of the invention is to provide for a process of preparing an improved thermostable spray dried rotavirus vaccine formulation that comprises of rotavirus strains in monovalent or multivalent rotavirus serotypes mixtures.

Yet another object of present invention is to prepare an improved thermostable spray dried powder or granule based rotavirus vaccine formulation.

Yet another object of present invention is to prepare an improved thermostable spray dried rotavirus vaccine formulation possessing properties ideal for filling and administration by oral delivery devices.

Yet another object of the present invention is to prepare an improved thermostable spray dried powder or granule based rotavirus vaccine formulation and blend it with blending agent to endow it with properties ideal for filling and administration by oral delivery devices.

Yet another object of the invention is to provide for a cost effective process to prepare a cost effective improved thermostable rotavirus vaccine formulation which can be afforded by the low income and developing world countries.

SUMMARY OF THE INVENTION

Accordingly, the present invention relates to an improved thermostable spray dried rotavirus vaccine formulation. The present invention further provides a spray drying process to obtain the improved thermostable spray dried rotavirus vaccine formulation. The said process being used for removing water moiety, one of the major sources of instability for aqueous rotavirus vaccine, from liquid rotavirus vaccine containing different serotypes either individually or in combination, to form dehydrated stable particles. The dehydration is accomplished by using spray drying methodology substituting destabilizing water interactions with stable interactions of formulation ingredients thereby providing a more thermostable vaccine made by a cost-effective process.

The improved thermostable spray dried rotavirus vaccine formulation can include live rotavirus strains selected from bovine, rhesus, human, ovine, rhesus/human reassortants, or bovine/human reassortants in monovalent or multivalent rotavirus serotype mixtures. The invention relates to the use of spray drying process using two-fluid nozzle spray drying method for atomization of the fluid through the nozzle using the atomization gas at appropriate pressure, flow rate, temperature of the drying and the pressurized atomization gas. The said drying and the pressurized gas are selected from Nitrogen, Argon, $CO_2$ or air or combinations thereof.

The thermostable rotavirus vaccine formulations thus obtained has potential to retain potency at high temperatures frequently encountered in developing and low income regions where majority of rotavirus burden exists and has potential to partially or completely eliminate the vaccine cold chain dependence. Thus the present invention discloses an improved thermostable rotavirus vaccine formulation with more heat-stability, reduced footprint, low-cost of transportation and ease of use features.

DETAILED DESCRIPTION OF THE INVENTION WITH ILLUSTRATIONS AND DRAWINGS

Figure 1:
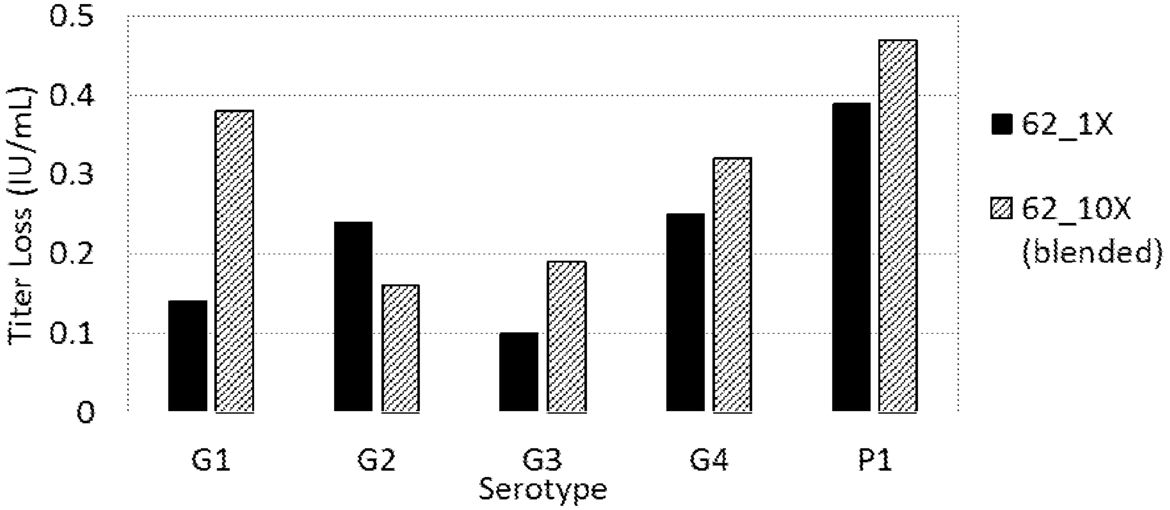
FIG. 1 depicts cumulative potency loss for the lead formulation SD 62 when spray dried at 1× dose and 10× dose.

In order to obviate the aforementioned drawbacks in the existing prior art, the present invention provides an improved thermostable spray dried rotavirus vaccine formulation. More particularly, the present invention provides an improved spray drying process to obtain said rotavirus vaccine formulation. More specifically the present invention discloses polyvalent thermostable rotavirus vaccine prepared by spray drying process, such that the said vaccine has improved heat-stability, ease-of-use, ease-of-transportation and affordability features with significantly better chance of being adopted in developing and low income country's vaccination program.

In order to rationally arrive at a spray drying process and formulations that best support process yield, thermostability and subsequent handling of the vaccine till administration, a fractional factorial Design of Experiment screening strategy has been employed to select amongst excipients/stabilizers and combinations thereof with respect to their ability to confer thermostability to single as well as multiple serotypes.

The said thermostable spray dried rotavirus vaccine formulations are obtained from the liquid vaccine formulations (feed) comprising of excipients and stabilizers that are "Generally Regarded As Safe" (GRAS) as defined by United States Food and Drug Administration (USFDA) and provide thermal stability to the rotavirus vaccines comprising monovalent and multivalent serotypes during and subsequent to spray drying as well as in liquid states obtained in before spray drying (feed) and after reconstitution of spray dried powder.

The said excipients and stabilizers are selected from—(a) sugars such as maltodextrin, sucrose, lactose, sorbitol, mannitol and trehalose; (b) divalent ionic protein structural stabilizers such as Zn (II) and Ca (II); (c) buffering agents such as 4-(2-hydroxyethyl)-1-piperazineethanesulfonic acid (HEPES), Tris, Phosphate or Histidine; (d) salts such as Sodium Chloride (NaCl); (e) bulking agents such as low particle size Sugar spheres/Pharma spheres (NPS), Maltodextrin, Sorbitol, Mannitol, Dextran or Lactose; (f) activating agents such as Arginine, Glutamic acid, sodium glutamate; (g) dispersants such as Tween 20 and Tween 80; and (h) surfactants such as sodium dodecyl sulfate (SDS), Poly ethylene glycol (PEG) 400, PEG-300, PEG-400 and PEG-600, Pluronic 68, and F127. In a preferred embodiment, said formulation of spray dried vaccine is formed using the liquid vaccine feed comprising: rotavirus serotype, 1% to 15% (w/v) either sucrose or trehalose or combinations thereof; 10 mM to 100 mM pH buffering component(s) or combinations thereof at a pH ranging from 6.0 to 8.0; 0.001% to 0.08% surfactants, 0.1 mM to 5 mM of a divalent cation, and 0.5% to 10% bulking agent.

The rotavirus vaccine formulation of the present invention comprises of at least one rotavirus serotypes in the range of $8.18\times10^6$ to $2.0\times10^6$ per dose administered, said at least one excipient in the range of 1% to 15% (w/v), said at least one buffering agent in the range of 10 mM to 100 mM, said at least one surfactant in the range of 0.001% to 0.08% and pH of 6-8.

The excipients and stabilizers, especially the buffering agents, are chosen to allow maximum solubility to the divalent ions, such as Zn (II) and Ca (II), which are principally required for maximum process stability and also play role in storage stability of rotaviruses at elevated temperatures for extended periods of time.

The excipients and their combinations are also chosen to generate powder characterized by glass transition temperature (Tg) higher than the intended storage temperature of the vaccine. The Tg of the formulations higher than the intended storage temperature suggest that those formulations will maintain rigid glassy state during storage at elevated temperatures that are below Tg.

The robustness of invention is dependent on its evaluation and validation by numerous analytical assays reporting critical quality attributes. The critical process parameters (CPP) for spray drying methodology are optimized to yield the critical quality attributes such as potency, yield, moisture, etc. as known in prior art affecting the stability and performance of a formulated vaccine. Thus in the present invention, responses monitored to Design of Experiment include potency measured by 'quantitative Reverse Transcriptase Polymerase Chain Reaction' (RT PCR) based Multivalent Quantitative Potency Assay, moisture content determination using Karl Fisher or gravimetric methods, thermal properties including glass transition temperature, flow and consolidation properties as well as visual observations of the spray dried material. Parameters like inlet temperature, aspiration, percent solids content have been evaluated as CPP to study their effect on critical quality attributes such as moisture, yield, particle size and outlet temperature.

To optimize the CPP, one example of the composition of virus free placebo formulation that is representative of final formulation and thus is useful for process optimization is presented in Table 1.

TABLE 1

Composition of Placebo Formulation useful for spray drying process optimization.

| Excipient | Composition |
|---|---|
| Sucrose | 1.765M |
| Sodium citrate | 235 mM |
| Sodium phosphate | 118 mM |
| pH | 6.2 |
| Water qs | 50 mL |

The present invention also discloses a method of spray drying accomplished using a 'two fluid nozzle' (binary nozzle) combining pressurized atomization gas and vaccine formulation in liquid form, hereinafter referred to as liquid vaccine formulation (feed).

The said two fluid nozzle spray drying method uses pressurized atomization gas at a pressure ranging from 4 bar to 7 bar and at a temperature ranging from 0° C. to 20° C. The drying and the pressurized gas for atomizing is selected from Nitrogen, Argon, $CO_2$ with purity not less than 95% v/v or air and moisture content not more than 2%. The drying gas is at a pressure that allows it to flow at the rate of 25 Nm3/h to 35 Nm3/h preferably 30 $Nm^3h$ for the specified scale of operation and equipment (e.g. Buchi B 290 advanced model) and at a temperature ranging from 0° C. to 200° C. with outlet temperatures ranging from 35° C. to 60° C.

The said spray drying process also involves the use of 'two fluid nozzle' for atomization of the fluid through the nozzle wherein nozzle orifice is adjusted from diameter 0.7 mm to 1.2 mm, preferably 1 mm, for the specified scale of operation and equipment (e.g. Buchi B 290 advanced model) to modulate the yield of >60% at particle size characterized by $D_{90}$~30 μm. Further the said binary nozzle is tuned to adjust the spray plume so as to yield maximum product contact with the drying gas and minimum losses leading to high product yields.

The said spray drying method uses the liquid feed solid contents in the range of 10.00 g/100 mL to 25.00 g/100 mL preferably around 21 g/100 mL for optimal drying and yield and the said liquid vaccine formulation (feed) is fed at a flow rate of 0.3 mL/min to 10.0 mL/min for the specified scale of operation. One example of the optimized process parameters is given in Table 2.

TABLE 2

Optimized process parameters that supports maximal yields and minimal moisture content.

| Parameter | Operating range | Optimal Values |
|---|---|---|
| Inlet temperature (° C.) | 0 to 200 | 70-75 |
| Outlet temperature (° C.) | 35 to 60 | 43-48 |
| Aspirator (%) | 65 to 80 | 70-75 |
| Feed rate (mL/min) | 0.3 to 10 | 0.4 |
| Spray gas flow (mm) | 25 to 35 | 30 |
| Atomization | 4 to 7 | 5 bar |
| Nozzle | Buchi two fluid std (0.7 mm-1.2 mm) | Buchi two fluid std (1 mm) |
| Cyclone | Buchi HP | Buchi HP |
| Feed solids (% w/v) | 10 to 25 | 21 |
| Dehumidifier | Yes | Yes |

The spray drying process using above optimized parameters and said compositions results in spray dried powder with improvements in the powder yield to >60% by preventing the losses in processing, particularly by preventing the material loss in equipment dead volume. The said pressurised atomization gases like Nitrogen or Argon with the above optimized parameters and said compositions results in spray dried powder with the residual moisture levels to <2% thereby preventing vaccine degradation pathways associated with presence of water as compared to using ambient or dehumidified air with residual moisture levels to >2%.

It is critical that the loss of vaccine antigen, both during processing and storage is avoided or kept at minimum to minimize cost of vaccine associated with antigen overfilling. Thus one of the critical criterion for a process and formulation is to reproducibly demonstrate acceptable potency losses [in this invention less than $Log_{10}$=[0.5]] when stored at 37° C. and analysed for at least 4 weeks thus satisfying World Health Organization's highest heat stability indicating VVM 30 criterion.

In order to economize the processing costs, the amount of time required for processing particular amount of material must be reduced. Thus spray drying at ten fold (10×) higher titre batch and further diluting the recovered concentrated powder 10 times with a blending agent can reduce the process time by 10 fold and increase the throughput of the process. Thus in one embodiment rotavirus serotypes used for spray drying comprises one or combinations of serotypes ranging from about $1\times10^4$ to $1\times10^9$ IU/mL and blended with bulking and/or buffering agent.

Additionally blending process, by allowing choice of blending agent with different physicochemical properties, gives an opportunity to engineer powder properties to appropriate for precise and reproducible weighing and filling g in different easy-to-use container closures. Thus in one embodiment the flow properties of the spray dried powder are improved using blending agents with ideal powder flow properties required for precise filling operations. The examples of blending agent that can be used for said powder engineering include sugars and sugar alcohols such as cyclodextrins, maltodextrin, dextrose, glucoses, mannitol starches, sorbitols, maltitols, xylitols and lactoses of various sizes and grades.

The improved thermostable spray dried rotavirus vaccine formulation of present invention comprises of single or multiple rotavirus serotypes with monovalent and multivalent strains of rotavirus is appropriately packed as monodose or multidose. The examples of easy-to-use packaging include sachet, dual chamber vials supplied with vaccine powder and diluent for reconstitution, where the spray dried rotavirus vaccine and dual chamber pouch/single container closure with a frangible seal that could be broken upon squeezing between fingers on diluents/buffer chamber allowing solid spray dried rotavirus vaccine and diluent to mix.

The use of the easy-to-use packaging increases the convenience of administration of the vaccine as well as reduce the risk of open manipulation/reconstitution of multicomponent vaccine. The reconstitution errors comprise of buffer/vaccine mismatch, wrong volumes, contamination etc. Moreover they have the potential of reducing the footprint of the vaccine easing the shipping as well as distribution challenges faced with traditional multi component primary packaging options such as separate vials for each component and associated syringes and adapters. The thermostable spray dried rotavirus vaccine powder thus obtained can also be formulated into a rapidly dispersible tablet dosage form.

In a preferred embodiment spray drying of the liquid pentavalent feed formulation is performed at higher virus titres for each of the rotavirus serotypes i.e G1, G2, G3, G4 & P1 preferably 10 times the quantities without adversely affecting the potency during process. In a particularly preferred embodiment the spray drying of the liquid pentavalent feed formulation is being performed at higher virus titres for a mixture the five serotypes i.e. G1, G2, G3, G4 & P1.

The thermostable spray dried rotavirus vaccine thus obtained, irrespective of serotypes and combinations thereof, when spray dried either at 1 fold (1×) dose level or blended vaccine formulation derived from the spray dried powders at 10× dose titre levels do not exceed the potency loss for at least 24 months at 2° C.-8° C. and also do not exceed the potency loss of $Log_{10}$ [0.5] when re-constituted in appropriate volume of the aqueous diluent and incubated at 2° C.-8° C. for 24 h, thereby facilitating administration of a multi-dose reconstituted vaccine for campaign setting and reducing wastage.

It is also desirable programmatically to have a powdered vaccine readily solubilize in diluent for administration to facilitate immunizing more subjects immunized in less time. Thus in one of the preferred embodiment the entire powder dose of the spray dried powder solubilize in water or aqueous solution is no more than 60 seconds.

It is critical for an oral administration vaccine to survive gastric acid. The vaccine is protected from stomach acid after oral administration by neutralizing stomach acid by incorporating Acid Neutralization Capacity (ANC) in spray dried vaccine as a buffer/antacid powder. The buffering/antacid component are selected from HEPES, citrate, histidine, calcium carbonate, sodium carbonate, potassium carbonate, sodium bicarbonate, calcium bicarbonate, potassium bicarbonate, aluminium hydroxide or magnesium hydroxide or combinations thereof. In a yet another preferred embodiment said spray dried rotavirus powder is blended with buffering agent and/or bulking agent resulting in acid neutralizing capacity in the range of 2.0 mEq/g to 5.0 mEq/g of powder.

Thus instant invention provides for a heat-stable, easy-to-use, easy-to-transport and affordable spray dried rotavirus vaccine that will impact the health of hundreds of millions of children in developing countries.

The person skilled in art would also recognize the applicability of the method and formulations to other virus including but not limited to measles virus, mumps virus, rubella virus, adenoviruses, influenza virus, respiratory syncytial virus, polio virus, herpes simplex virus, Epstein-Bar virus. Similarly, the method and formulations would applicable to bacteria including but not limited to *Mycobacterium, Pneumococcus, Salmonella, Shigella, Listeria, E. Coli, Streptococcus, Pseudomonas, Staphylococcus* and *Vibrio*.

The following examples illustrate but do not limit the scope of invention.

Example 1

Effect of Spray Drying on the Stability of Rotavirus Serotypes

An exemplified lead formulation SD 62 (Table 3) containing 5 human-bovine rotavirus serotypes G1, G2, G3, G4 & P1 has been prepared with virus titres of 0.818×$10^7$ for each of the serotypes.

TABLE 3

Composition of DoE formulations evaluated for spray drying thermo-stabilization of rotavirus vaccine formulation containing rotavirus serotypes G1, G2, G3, G4 & P1.

| Ingredient | SD 62 (g/100 ml) | SD 63 (g/100 ml) | SD 64 (g/100 ml) | SD 65 (g/100 ml) | SD 66 (g/100 ml) |
|---|---|---|---|---|---|
| Maltodextrin | 9 | 6 | 6 | 9 | 9 |
| Sorbitol | 2.5 | 2.5 | 2.5 | 2.5 | 0 |
| NaCl | 0.88 | 0.88 | 0.88 | 0.88 | 0.88 |
| Glutamic acid | 0.131 | 0.131 | 0.131 | 0.131 | 0.131 |
| Trehalose | 7 | 10 | 10 | 7 | 10 |
| Histidine | 20 mM | 20 mM | 30 mM | 30 mM | 30 mM |
| $CaCl_2$ | 2 mM | 2 mM | 3 mM | 3 mM | 3 mM |
| HEPES | 25 mM | 25 mM | 37.5 mM | 37.5 mM | 37.5 mM |
| Water q.s. | 100 | 100 | 100 | 100 | 100 |
| Solids (%) | 20.44 | 20.44 | 20.9 | 20.9 | 21.4 |
| pH | 6.2 | 6.2 | 6.2 | 6.2 | 6.2 |

The pH of the feed solution has been adjusted to 6.2 with 0.1N HCl or NaOH. The spray drying has been carried out at an inlet temperature of 70° C.-75° C., outlet temperature of 43° C.-48° C. with aspirator operating at 70-75%. The feed rate has been kept 0.4-1.0 mL/min and with feed solids of 17-20.45% g/mL with a spray gas flow of 30 $Nm^3$/hr and atomization pressure of 5 bar. The spray nozzle used is being Buchi two fluid (0.7 mm) and the cyclone used to collect the powder is being Buchi HP. Recovery of the collected powder has been performed under low RH (<5%) conditions.

a) Study 1: The recovered spray dried powder has been tested for instant moisture content using a Mettler Toledo Halogen balance or/& a Karl Fischer titrator and have been found to have moisture content of <2.0%.

b) Study 2: The recovered spray dried powder has been reconstituted with MilliQ water at a concentration of 150 mg/mL and tested for process loss in comparison with liquid control (stored at −70° C.) and have been found to incur losses that are statistically same as zero.

c) Study 3: The remaining recovered spray dried powder have been sealed in glass vials, and stored for at least 4 weeks at 37° C./75% RH in stability chambers. These samples have been reconstituted at a concentration of 150 mg/mL and tested for stability loss and have been found to incur losses not exceeding $Log_{10}$ [0.5] IU/mL at 1× dose (FIG. 1 filled bars).

Example 2

Effect of Spray Drying Rotavirus Serotypes at High Virus Litres and Subsequent Blending on the Potency of Spray Dried Rotavirus Powders The exemplified lead formulation SD 62 composition, containing 5 human-bovine rotavirus serotypes G1, G2, G3, G4 & P1 has been prepared at high virus titres of 8.18×$10^7$ (10× Dose) IU/ml. The pH of the feed solution has been adjusted to 6.2 with 0.1N HCl or NaOH. The spray drying and sample processing has been conducted as described in Example 1.

a) Study 1: The recovered spray dried powder has been blended with bulking agent and/or buffering agent maltodextrin (DE 4-7) to yield viral tiers equal to 1.0× dose as described in Example 1. The bulking agent and/or buffering agent have been prepared as per the composition shown in the table 4.

TABLE 4

Composition of the bulking agent and/or buffering agent for lead formulation SD 62

| | |
|---|---|
| Spray dried powder (10X) | 10% |
| Maltodextrin | 83.97% |
| HEPES | 3.84% |
| Histidine | 2.00% |
| Calcium chloride | 0.19% |

b) Study 2: The recovered unblended and blended spray dried powder have been tested for instant moisture content using a Mettler Toledo Halogen balance or/& a Karl Fischer titrator and have been found to have moisture content of <2.0%.

c) Study 3: The recovered blended spray dried powder, with a concentration of 150 mg/mL along with liquid control (stored at −70° C.), has been reconstituted and tested for process loss and have been found to incur losses that have not been statistically different than zero.

d) Study 4: The recovered blended spray dried powder has been sealed in glass vials, and stored for at least 4 weeks at 37° C./75% RH in a stability chamber. These samples have been reconstituted with a concentration of 150 mg/mL and tested for stability loss. All samples have been found to incur losses not exceeding $Log_{10}$ [0.5] IU/mL, not less than 2×$10^6$ in 150 mg at 10× dose (FIG. 1 striped bars).

Example 3

Figure 2:
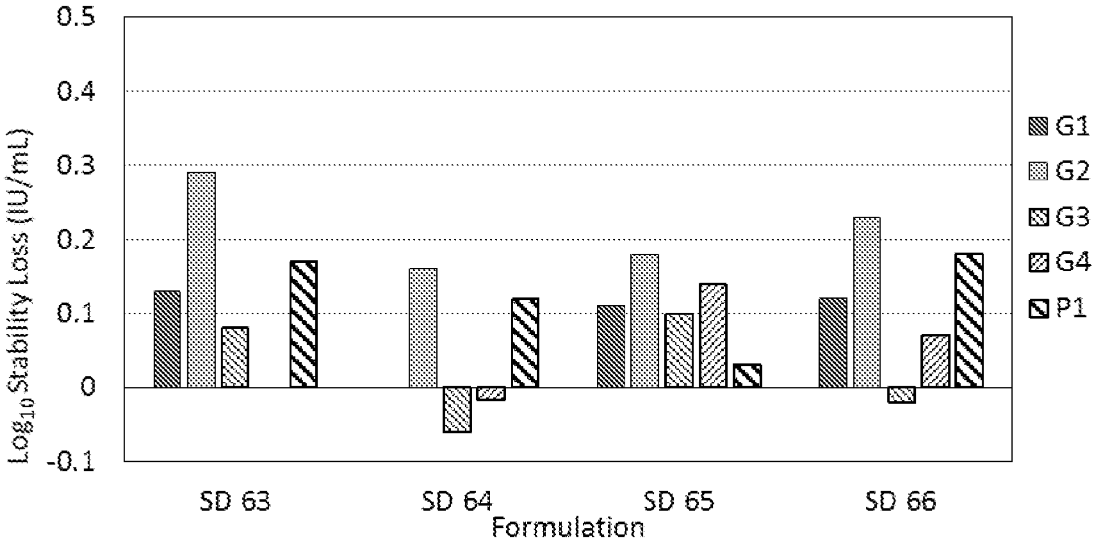
FIG. 2 depicts DoE blended 10× batches Process plus Stability loss for 8 weeks.
Figure 3:
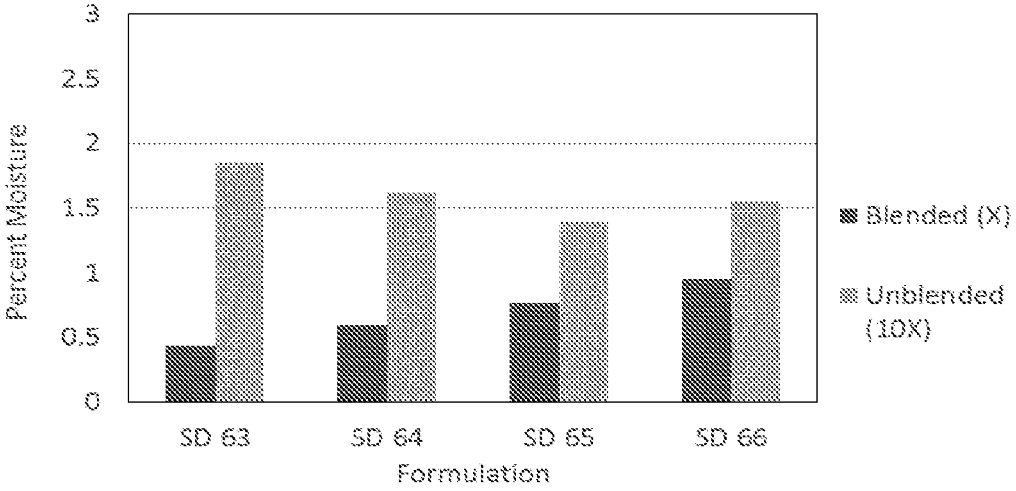
FIG. 3 depicts moisture content comparison of Blended and Unblended powder samples.
Figure 4:
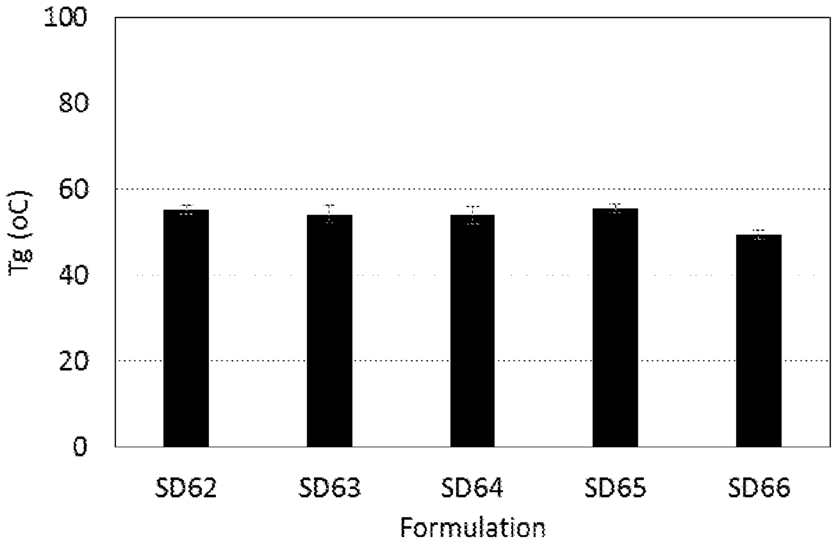
FIG. 4 depicts glass transition temperatures of DoE batches (Unblended, 10× Rotavirus vaccine formulations).

Effect of Sugar, Buffer and Cations on Thermostabilization of Spray Dried Rotavirus Serotypes The composition exemplified lead formulation SD 62 has been further modified and tested at different concentration of ingredients to generate the exemplified pentavalent formulations SD 63, SD 64, SD 65 & SD 66 (Table 3). These formulations containing 5 human-bovine rotavirus serotypes G1, G2, G3, G4 & P1 have been prepared with virus titres of $8.18 \times 10^7$ (10× Dose) IU/ml. The spray drying is being carried out as described in Example 1. The recovered spray dried powder has been blended with bulking agent and/or buffering agent to yield viral tiers equal to 1.0× dose as described in Example 2 and table 4.

a) Study 1: The recovered unblended and blended spray dried powder, with a concentration of 150 mg/mL along with liquid control (stored at −70° C.), has been reconstituted and tested for process loss (and have been found to incur losses that have not been statistically different than zero.

e) Study 2: The recovered unblended and blended spray dried powder have been sealed in glass vials, and stored for at least 4 weeks at 37° C./75% RH in a stability chamber. These samples with a concentration of 150 mg/mL have been reconstituted and tested for stability loss (FIG. 2).

b) Study 3: The recovered unblended and blended spray dried powders have been tested for instant moisture content using a Karl Fischer titrator (FIG. 3). The spray dried samples have been characterized by moisture content less than 2.0% while blended samples exhibited moisture content of 0.44% to 0.95%.

c) Study 4: A 20 mg of recovered unblended spray dried powder has been tested for Glass transition temperature (Tg) using Differential Scanning calorimetry (DSC). The Tg of the spray dried powders is reported as the midpoint temperature and particle size distribution (FIG. 4).

d) Study 5: Particle size distribution (PSD) of the unblended, control (maltodextrin alone) and blended powder mixes, dispersed in a suitable anti-solvent, has been determined using Malvern Mastersizer 3000. The D90, D50 and D10 values for potential batches are shown in Table 5.

TABLE 5

Particle size distribution of the unblended, and blended exemplified formulations and its comparison to maltodextrin bulking agent

| | | SD63 | | SD64 | | SD 66 | |
|---|---|---|---|---|---|---|---|
| Parameter | Maltodextrin | Unblended | Blended | Unblended | Blended | Unblended | Blended |
| D10 | 23.39 | 1.49 | 19.71 | 1.22 | 19.76 | 1.91 | 25.12 |
| D50 | 69.84 | 11.24 | 70.26 | 11.79 | 70.21 | 13.29 | 76.57 |
| D90 | 145.66 | 23.06 | 144.06 | 23.93 | 142.91 | 24.36 | 154.21 |

Example 4

Effect of Spray Drying Parameters on Powder Properties of Spray Dried Exemplified Lead Formulation Study 1: Determination of Flow and consolidation properties of the lead formulation: The exemplified lead formulation SD 64 containing 5 human-bovine rotavirus serotypes have been spray dried at virus titers of $8.18 \times 10^7$ (10× Dose) IU/mL. The pH of the feed solution has been adjusted to 6.2 with 0.1N HCl or NaOH. The spray drying has been carried out as described in Example 1. The recovered spray dried powder has been blended with bulking agent and/or buffering agent to yield viral tiers equal to 1.0× dose as described in Example 2 and table 4.

A 5.16 g of powder has been transferred to a 50 mL graduated cylinder to measure the bulk volume occupied and calculate the bulk density. Further the cylinder has been tapped as per the USP till the difference in the volume tapped volumes of individual set of tappings is less than 2%. The tapped volume has been measured to calculate the tapped density. The consolidation properties such as Carr's/Consolidation Index and Hausner's ratio have been derived, the values of which are shown in Table 6. The values indicate a fair to passable flow characteristics of the powder as categorized in USP.

TABLE 6

The flow characteristics of the lead formulation SD 64

| Flow Parameter | Values |
|---|---|
| $W_b$ | 5.16 g |
| $V_{bulk}$ | 11.4 mL |
| BD | 0.448 |
| $V_{tapped}$ (USP) | 9.0 mL |
| TD | 0.573 |
| Carr's Index | 21.8 |
| Hausner Ratio | 1.27 |

Study 2: Determination of Dissolution Time in Lead Formulation SD 64:

The exemplified lead formulation SD 64 containing 5 human-bovine rotavirus serotypes have been spray dried at virus titres of $8.18 \times 10^7$ (10× Dose) IU/ml. The pH of the feed solution has been adjusted to 6.2 with 0.1N HCl or NaOH. The spray drying has been carried out as described in Example 1. The recovered spray dried powder has been blended with bulking agent and/or buffering agent to yield viral tiers equal to 1.0× dose as described in Example 2 and table 4.

The blended spray dried powder has been accurately weighed in a vial under a low RH (<5%) nitrogen environment approximately. This powder water is being added to a concentration of 150 mg/2 mL to 200 mg/2 mL and the vial shaken manually to observe the dissolution. The elapsed time between the addition of the water and the point at which no particulate is visible in solution has been recorded as the dissolution time. The rate of solubilisation of the lead formulation SD 64 is shown in Table 7.

TABLE 7

The rate of solubilization of the spray dried powder in water in SD 64

| | Unblended (10X) spray dried powder | | Blended (1 Part of 10X spray dried powder diluted with 9 parts of bulking agent) | |
|---|---|---|---|---|
| S. No | Dissolution Time (150 mg in 2 mL) (In seconds) | Dissolution Time (200 mg in 2 mL) (In seconds) | Dissolution Time (150 mg in 2 mL) (In seconds) | Dissolution Time (200 mg in 2 mL) (In seconds) |
| 1 | 43 | 48 | 20 | 13 |
| 2 | 42 | 50 | 14 | 19 |

TABLE 7-continued

The rate of solubilization of the spray dried powder in water in SD 64

| S. No | Unblended (10X) spray dried powder | | Blended (1 Part of 10X spray dried powder diluted with 9 parts of bulking agent) | |
|---|---|---|---|---|
| | Dissolution Time (150 mg in 2 mL) (In seconds) | Dissolution Time (200 mg in 2 mL) (In seconds) | Dissolution Time (150 mg in 2 mL) (In seconds) | Dissolution Time (200 mg in 2 mL) (In seconds) |
| 3 | 48 | 52 | 13 | 18 |
| Average (n = 3) | 44 ± 3 | 50 ± 2 | 16 ± 3 | 17 ± 3 |

Example 5

Effect of Spray Drying of Rotavirus Serotypes in Exemplified Lead Formulation SD 64 on Potency after Reconstitution The exemplified lead formulation SD 64 containing 5 human-bovine rotavirus serotypes have been spray dried at virus titres of $8.18\times10^7$ (10× Dose) IU/mL. The pH of the feed solution has been adjusted to 6.2 with 0.1N HCl or NaOH. The spray drying is being carried out as described in Example 1. The recovered spray dried powder has been blended with bulking agent and/or buffering agent to yield viral tiers equal to 1.0× dose as described in Example 2 and table 4.

The 150 mg blended powder has been dissolved in 2 mL water and stored for at least 24 hours at 37° C./75% RH and 2-8° C. in a stability chamber. The potency loss of the lead formulation at different temperatures for 24 hours is shown in Table 8.

TABLE 8

The potency loss of spray dried rotavirus serotypes at different temperatures for 24 hours.

| Serotype | LOG LOSS at 2-8° C. for 24 h | LOG LOSS at 37° C. for 24 h |
|---|---|---|
| G1 | 0.09 ± 0.07 | 0.33 ± 0.16 |
| G3 | 0.17 ± 0.09 | 0.70 ± 0.17 |

Example 6

Determination of Acid Neutralization Capacity (ANC) of the Exemplified Lead Formulation SD 64

The exemplified lead formulation SD 64 containing 5 human-bovine rotavirus serotypes have been spray dried at virus titres of $8.18\times10^7$ (10× Dose) IU/mL. The pH of the feed solution has been adjusted to 6.2 with 0.1N HCl or NaOH. The spray drying is being carried out as described in Example 1. The recovered spray dried powder has been blended with bulking agent and/or buffering agent to yield viral tiers equal to 1.0× dose as described in Example 2 and table 4.

The Acid Neutralization Capacity (ANC) of the blended spray dried powder has been determined as per USP. Briefly, 150 mg of the blended powder has been dissolved in 70 mL of water and the solution has been stirred for 1 min. Then 30 mL of 1N HCl has been added to this sample solution and again the solution has been stirred for exactly 15 mins and in period not to exceed an additional 5 minutes. The excess HCl has been titrated with 0.5N NaOH to attain a stable (10-15 seconds) pH of 3.5. The number of milli-equivalents of the acid consumed by the powder has been calculated by the formula; Total $mEq=(30\times N_{HCl})-V_{NaOH}-N_{NaOH})$. The ANC has been calculated and is the results are shown in Table 9.

TABLE 9

ANC for composition number SD 64.

| S. No. | Powder (Blended) | ANC (mEq/dose powder) |
|---|---|---|
| 1 | SD 64 | 0.49 |
| 2 | SD 64 | 0.46 |
| 3 | SD 64 | 0.48 |
| Average ANC (mEq of acid consumed per dose powder) of 3 determinations | | 0.476 |

Example 7

Determination of Extended Longitudinal Thermostability

Figure 5A:
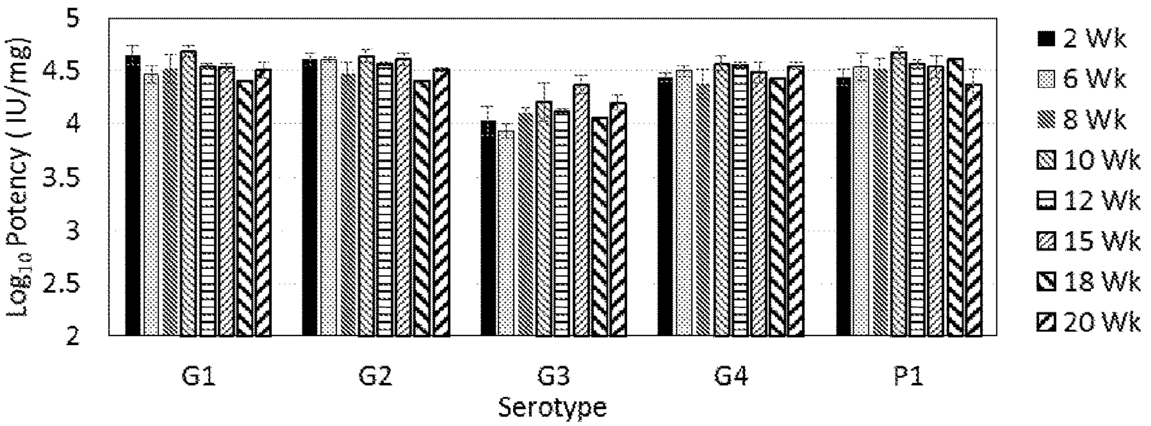
FIG. 5A depicts potency changes of five rotavirus spray dried serotypes stored at 4° C. for indicated amount of times in a lead formulation SD 64.
Figure 5B:
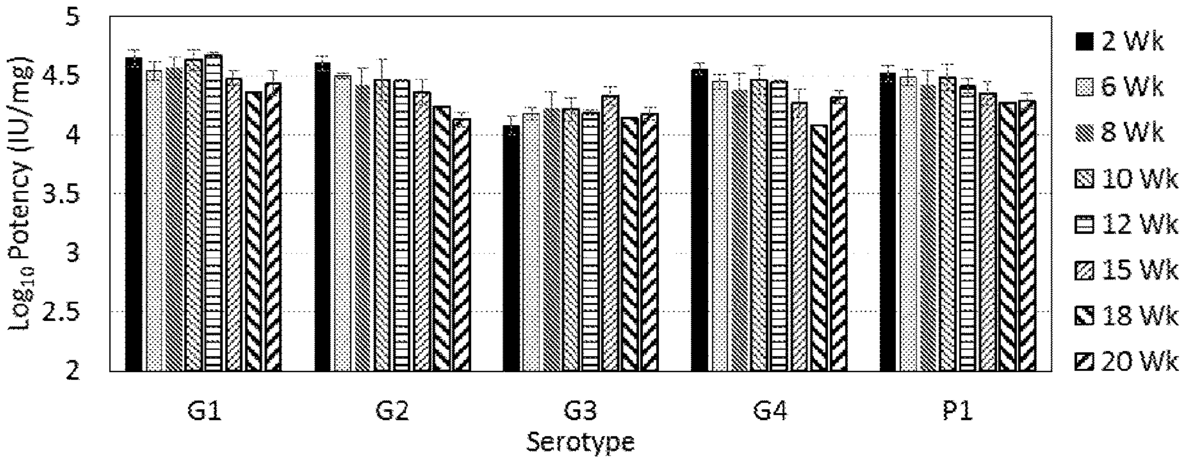
FIG. 5B depicts potency changes of five rotavirus spray dried serotypes stored at 37° C. for indicated amount of times in a lead formulation SD 64.
Figure 6A:
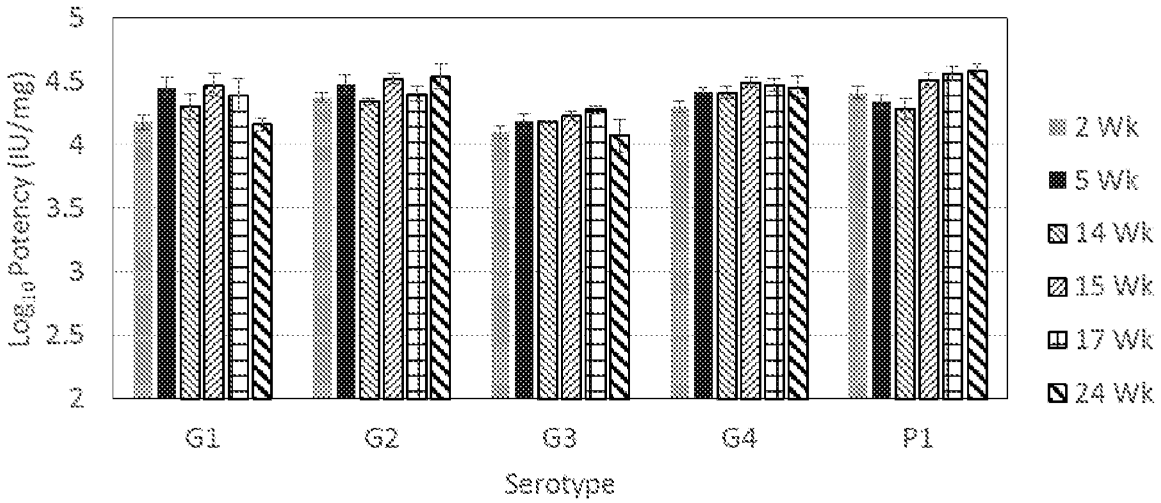
FIG. 6A depicts SD 66 retains potency for 24 weeks at 4° C.
Figure 6B:
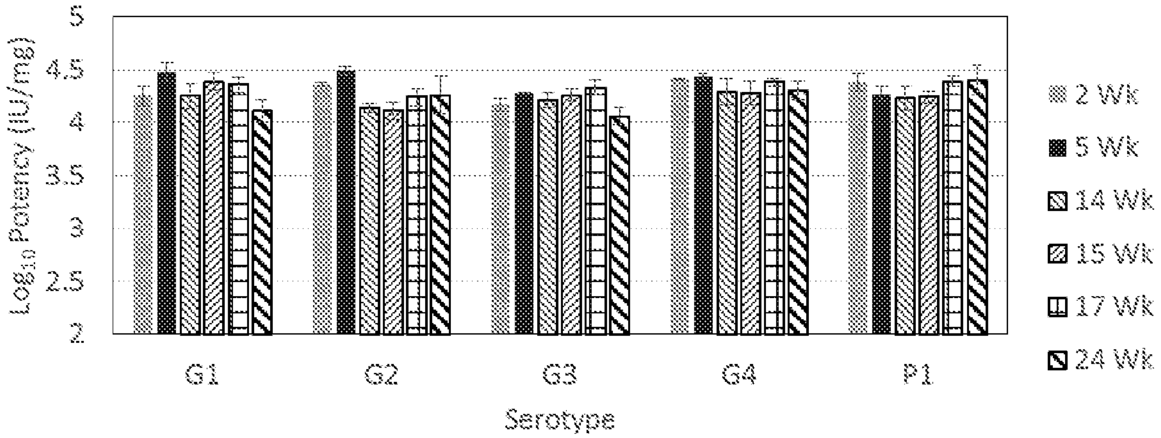
FIG. 6B depicts SD 66 retains its potency for 24 weeks at 37° C.

The exemplified formulations SD64 and SD66 have been prepared with the process outlined in Example 2 and tested for the process and stability loss of virus titre and have been found to exhibit statistically no process loss and retain its potency for 20 weeks (FIGS. 5 A and 5B) to 24 weeks (FIGS. 6A and 6B) at 4° C. and 37° C. respectively.

Example 8

Reproducibility of Spray Drying Process

Figure 7A:
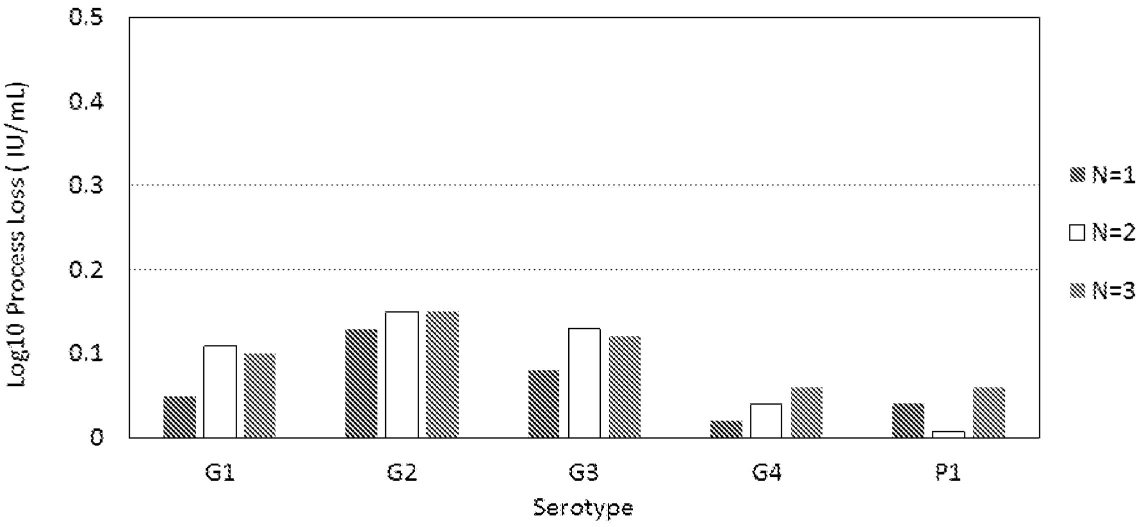
FIG. 7 A depicts process loss comparison of SD 64 reproducibility batches.
FIG. 7B depicts process loss comparison of SD 66 reproducibility batches.
Figure 7B:
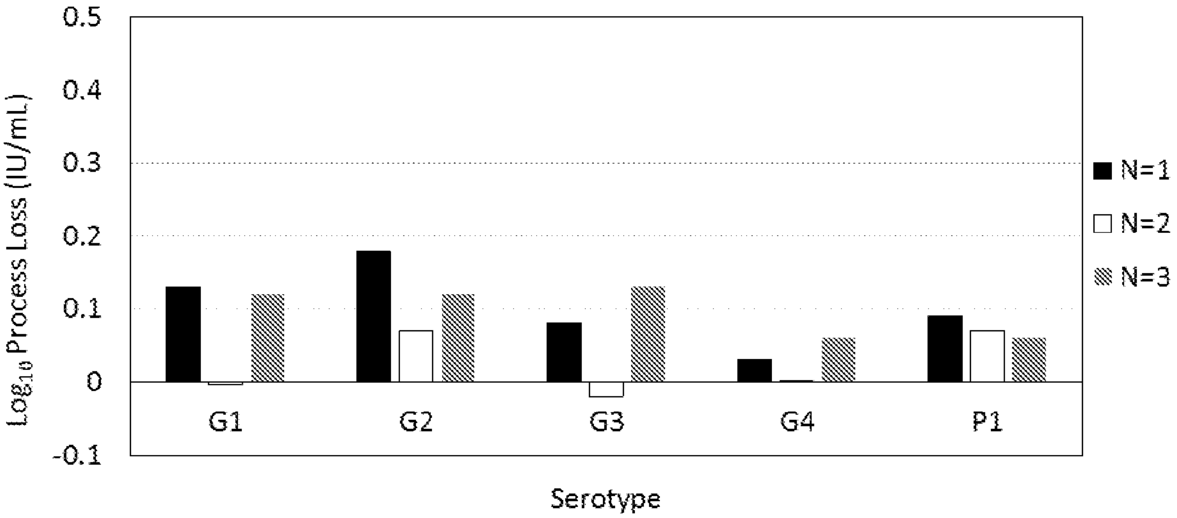
Figure 8:
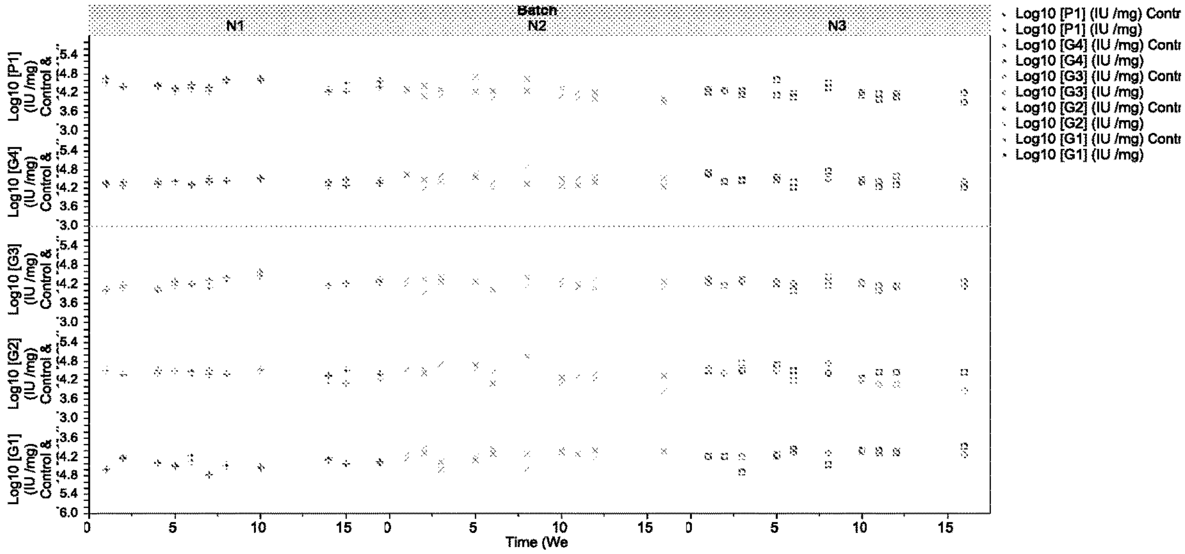
FIG. 8 depicts SD 66 reproducibly retains potency for 16 weeks when incubated at 4° C. and 37° C.

The reproducibility trials have been conducted on exemplified lead formulation SD 64 and SD 66 with samples prepared as outlined in Example 7. The results for the process loss from said three trials, i.e. N=1, 2, 3 have been compared (FIGS. 7A and 7B). The results for reproducible potency retention in SD 66 for at least 16 weeks in three batches at 37° C. are summarized in FIG. 8.

Example 9

Effect of High Temperatures on Rotavirus Potency in Exemplified Spray Dried Formulation Compositions SD 64 and SD 66

The exemplified lead formulation SD 64 and SD 66 have been tested for stability losses at 45° C. to determine their suitability in transport in 'Controlled Temperature Chain' wherein vaccine is transported outside cold chain for the last mile of immunization supply potentially exposing vaccine to temperatures >40° C. The SD 64 and SD 66 formulations containing five human-bovine rotavirus serotypes have been prepared at virus titres of $8.18\times10^7$ (10× Dose) IU/ml. The pH of the feed solution has been adjusted to 6.2 with 0.1N HCl or NaOH. The spray drying has been carried out as described in Example 1. The recovered spray dried powder has been blended with bulking agent and/or buffering agent to yield viral tiers equal to 1.0× dose as described in Example 2 and table 4.

Figure 9A:
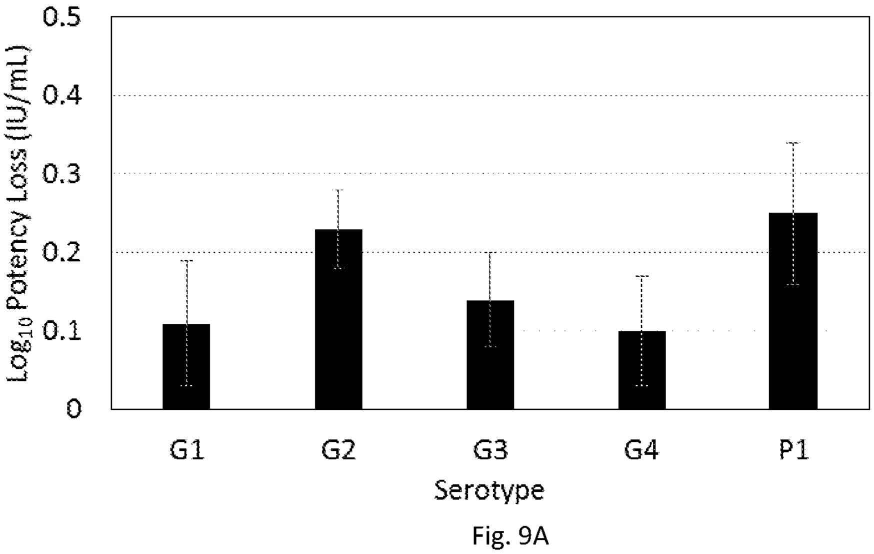
FIG. 9A and FIG. 9B depicts SD 64 and SD 66 retains potency at 45° C. for two and four weeks respectively.
Figure 9B:
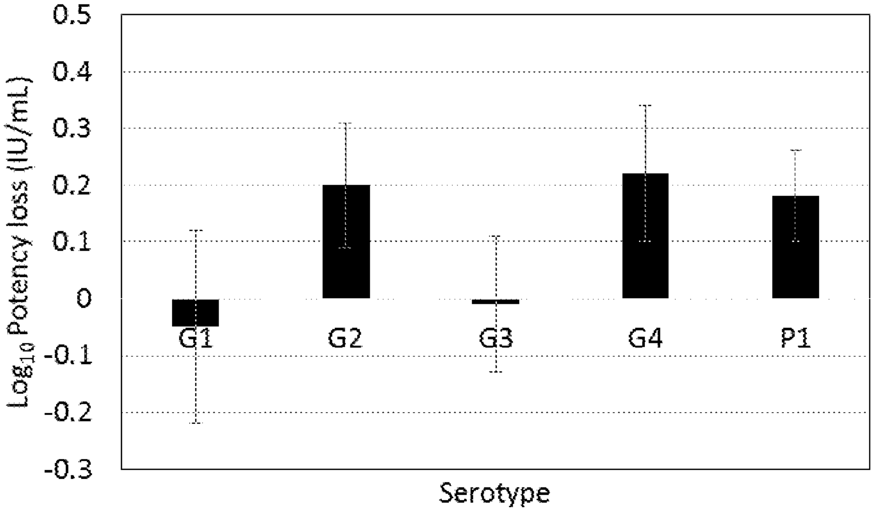

The recovered unblended and blended spray dried powder have been tested for instant moisture content using a Mettler Toledo Halogen balance or/& a Karl Fischer titrator (FIG. 4). The recovered unblended and blended spray dried powder, with a concentration of 150 mg/mL along with liquid control is stored at −70° C. The recovered unblended and blended spray dried powder have been sealed in glass vials, and stored for at least 2 weeks at 45° C./75% RH and 2-8° C. in a stability chamber. The SD 64 and SD 66 samples with a concentration of 150 mg/mL have been reconstituted and tested for potency loss (FIG. 9 A and FIG. 9B) and found to exhibit potency losses lower than $Log_{10}$=[0.5].

We claim:

1. A thermostable spray dried rotavirus vaccine formulation comprising:
- at least one rotavirus serotype
- a sugar, a buffering agent, a structural stabilizer, a salt, a bulking agent, and an activating agent,
- wherein
- the sugar is trehalose or sucrose or a combination thereof at 1-15% (w/v);
- the buffering agent is HEPES or histidine or a combination thereof at 10-100 mM;
- the structural stabilizer is $Ca^{2+}$ at 0.1-5 mM;
- the salt is sodium chloride at 0.88% (w/v);
- the bulking agent is maltodextrin at 0.5-10% (w/v); and
- the activating agent is glutamic acid at 0.131% (w/v);

and wherein the spray dried formulation exhibits potency losses of less than Log 10=[0.5] when stored at 37° C. for 4 weeks.

2. The thermostable spray dried rotavirus vaccine formulation as claimed in claim 1 wherein said rotavirus serotype is selected from at least one rotavirus strains being selected from bovine, rhesus, human, ovine, rhesus/human reassortants, or bovine/human reassortants.

3. The thermostable spray dried rotavirus vaccine formulation as claimed in claim 1 wherein said rotavirus serotype is selected from the human-bovine rotavirus ressortants serotypes G1, G2, G3, G4, and P1 either alone or in combination.

4. The thermostable spray dried rotavirus vaccine formulation as claimed in claim 1 further comprising an antacid selected from HEPES, citrate, histidine, calcium carbonate, sodium carbonate, potassium carbonate, sodium bicarbonate, calcium bicarbonate, potassium bicarbonate, aluminium hydroxide, and magnesium hydroxide with acid neutralizing capacity in the range of 0.4 to 0.5 meq/dose.

5. The thermostable spray dried rotavirus vaccine formulation as claimed in claim 1 wherein said rotavirus serotypes titre is $0.818\times10^{7}$ IU/mL in 1× dose and $8.18\times10^{7}$IU/mL in 10× dose.

6. The thermostable spray dried rotavirus vaccine formulation as claimed in claim 1 wherein said vaccine formulation is powder or granule based formulation.

7. A process of preparing thermostable spray dried rotavirus vaccine formulation as claimed in claim 1, said process comprising the steps of:
- (a) selecting said at least one rotavirus serotype;
- (b) adding said sugar, buffering agent, structural stabilizer, salt, bulking agent and activating agent to said selected rotavirus serotype of step (a) to prepare a liquid feed; and
- (c) spray drying of said liquid feed of step (b) in a spray dryer with a two-fluid nozzle using an atomization gas at predetermined process parameters to obtain a spray dried rotavirus vaccine formulation, wherein said process parameters and their operational range comprises

| Process parameters | operational range |
|---|---|
| Inlet temperature | 0 to 200° C. |
| Outlet temperature | 35° C. to 60° C. |
| Aspirator | 65 to 80% |
| Feed rate | 0.3 mL/min to 10 mL/min |
| Spray gas flow | 25 $Nm^3$/hr to 35 $Nm^3$/hr |
| Atomization pressure | 4 bar to 7 bar |
| Nozzle orifice diameter | 0.7 mm to 1.2 mm |
| Feed solids | 10% g/mL to 25% g/mL. |

8. The process of preparing thermostable spray dried rotavirus vaccine formulation as claimed in claim 7 wherein said process parameters and their range comprises

| Process parameters | range |
|---|---|
| Inlet temperature | 70° C. to 75° C. |
| Outlet temperature | 43° C. to 48° C. |
| Aspirator | 70% to 75% |
| Feed rate | 0.4 mL/min |
| Spray gas flow | 30 $Nm^3$/hr |
| Atomization pressure | 5 bar |
| Nozzle orifice diameter | 1 mm |
| Feed solids | 21% g/mL. |

9. The process of preparing thermostable spray dried rotavirus vaccine formulation as claimed in claim 8 wherein said atomization gas being selected from Nitrogen, Argon, Carbon dioxide or atmospheric air or combinations thereof, with purity of not less than 95% v/v and moisture content not more than 2%.

10. The process of preparing thermostable spray dried rotavirus vaccine formulation as claimed in claim 7 wherein said vaccine formulation is stable for 24 hours after reconstitution.

11. The thermostable spray dried rotavirus vaccine formulation as claimed in claim 1 wherein said thermostable spray dried rotavirus vaccine comprises formulation SD66 and maintains potency with potency loss of less than $Log_{10}$=[0.5] for 4 weeks at 37° C. and for 24 months at 2° C. to 8° C.

12. The thermostable spray dried rotavirus vaccine formulation as claimed in claim 1 wherein said thermostable spray dried rotavirus vaccine comprises formulation SD66 and maintains potency with potency loss of less than $Log_{10}$=[0.5] for 24 weeks at 37° C. and for 24 months at 2° C. to 8° C.

13. The thermostable spray dried rotavirus vaccine formulation as claimed in claim 1 wherein said thermostable spray dried rotavirus vaccine comprises formulation SD66 and maintains potency with potency loss of less than $Log_{10}$=[0.5] for 4 weeks at 45° C., 24 weeks at 37° C. and for 24 months at 2° C. to 8° C.

14. The thermostable spray dried rotavirus vaccine formulation as claimed in claim 1 wherein said vaccine formulation comprising of single or multiple rotavirus serotypes with monovalent and multivalent strains of rotavirus is appropriately packed as monodose or multidose.

15. The process of preparing thermostable spray dried rotavirus vaccine formulation as claimed in claim 7, further comprising the step of blending of said spray dried rotavirus vaccine formulation of step (c) with said at least one blending agent to obtain a dispersible form of said spray dried rotavirus vaccine formulation.

16. The process of preparing thermostable spray dried rotavirus vaccine formulation as claimed in claim 15 wherein said blending is being carried out with said blending agent either alone or in combination with said antacid in a manner wherein said blending agent individually or in combination with said antacid confers Tg of not less than 50° C., said antacid in acid neutralizing capacity in the range of 2.0 mEq/g to 5.0 mEq/g of powder.

* * * * *